(12) United States Patent
Vasireddy et al.

(10) Patent No.: US 8,049,009 B2
(45) Date of Patent: Nov. 1, 2011

(54) PROCESS FOR THE PREPARATION OF TENOFOVIR

(75) Inventors: Uma Maheswer Rao Vasireddy, Andharapradesh (IN); Siva Rama Prasad Vellanki, Andharapradesh (IN); Raja Babu Balusu, Andharapradesh (IN); Naga Durga Rao Bandi, Andharapradesh (IN); Pavan Kumar Jujjavarapu, Andharapradesh (IN); Sambasiva Rao Ginjupalli, Andharapradesh (IN); Rama Krishna Pilli, Andharapradesh (IN)

(73) Assignee: Matrix Laboratories Ltd., Secunderabad (IN)

( * ) Notice: Subject to any disclaimer, the term of this patent is extended or adjusted under 35 U.S.C. 154(b) by 384 days.

(21) Appl. No.: 12/352,182

(22) Filed: Jan. 12, 2009

(65) Prior Publication Data

US 2009/0286981 A1   Nov. 19, 2009

Related U.S. Application Data

(63) Continuation-in-part of application No. PCT/IN2007/000286, filed on Jul. 11, 2007.

(51) Int. Cl.
  *C07F 9/6561* (2006.01)
(52) U.S. Cl. ...................................................... 544/244
(58) Field of Classification Search .................. 544/244
  See application file for complete search history.

(56) References Cited

U.S. PATENT DOCUMENTS

| 5,733,788 | A | * | 3/1998 | Bischofberger | 436/98 |
| 5,922,695 | A | * | 7/1999 | Arimilli et al. | 514/81 |
| 6,465,649 | B1 | * | 10/2002 | Gutierrez et al. | 544/244 |
| 2004/0018150 | A1 | * | 1/2004 | Becker et al. | 424/9.1 |
| 2009/0176983 | A1 | * | 7/2009 | Dova et al. | 544/242 |
| 2009/0270352 | A1 | * | 10/2009 | Dova et al. | 514/81 |
| 2011/0009368 | A1 | * | 1/2011 | Dova | 514/81 |

FOREIGN PATENT DOCUMENTS

| IN | 2008MU00292 A | * | 10/2009 |
| WO | WO 2008007392 A2 | * | 1/2008 |

* cited by examiner

*Primary Examiner* — Mark Berch
(74) *Attorney, Agent, or Firm* — Ladas & Parry LLP

(57) ABSTRACT

The present invention relates to novel Tenofovir disoproxil hemifumarate salt, which is prepared by dealkylation of Phosphonate esters by using mineral acids followed by esterification and crystallization to give crystalline Tenofovir disoproxil. The Tenofovir disoproxil is further converted to fumarate salts with improved yield.

13 Claims, 8 Drawing Sheets

PROCESS FOR THE PREPARATION OF TENOFOVIR

The present application is a continuation-in-part of International Application PCT/IN2007/000286, with an international filing date of Jul. 11, 2007.

FIELD OF INVENTION

The present invention relates to novel Tenofovir disoproxil hemifumarate salt, which is prepared by dealkylation of Phosphonate esters by using mineral acids followed by esterification and crystallization to give crystalline Tenofovir disoproxil. The Tenofovir disoproxil is further converted to fumarate salts with improved yield.

BACKGROUND OF THE INVENTION

Tenofovir disoproxil is chemically known as 9-[-2-(R)-[[bis[[(isopropoxycarbonyl)oxy]methoxy]phosphinoyl]methoxy]propyl]adenine represented by the following structure:

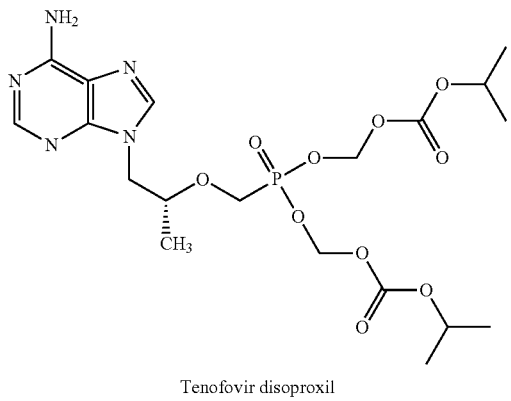

Tenofovir disoproxil

The above compound is a highly potent antiviral agent, particularly for the therapy or prophylaxis of retroviral infections and belongs to a class of drugs called Nucleoside Reverse Transcriptase Inhibitors (NRTI) which blocks reverse transcriptase an enzyme crucial to viral production in HIV-infected people. These are related to Nucleoside Reverse Transcriptase Inhibitors (NRTI).

U.S. Pat. No. 5,733,788 discloses the process for the preparation of (R)-9-[2-(phosphonomethoxy)propyl]adenine which involves condensation of (R)-9-[2-(hydroxyl)propyl]adenine and Diethyl p-toluenesulfonyloxy methylphosphonate in presence of Lithium hydride in Dimethylformamide followed by dealkylation with Bromotrimethylsilane in Acetonitrile.

U.S. Pat. No. 5,922,695 discloses the synthetic route for the preparation of (R)-9-[2-(phosphonomethoxy)propyl]adenine by condensation of (R)-9-[2-(hydroxyl)propyl]adenine with diethyl p-toluenesulfonyloxymethyl phosphonate in presence of lithium tert-butoxide in tetrahydrofuran followed dealkylation with bromotrimethylsilane in acetonitrile. Further, Tenofovir disoproxil base is obtained as oil which is further converted to fumarate salt.

US 2004/0018150 discloses a process for the preparation of (R)-9-[2-(phosphonomethoxy)propyl]adenine where diethyl p-toluenesulfonyloxymethyl phosphonate is condensed with (R)-9-[2-(hydroxyl)propyl]adenine in presence of Magnesium isopropoxide or Magnesium tert-butoxide in dimethylformamide medium followed by dealkylation with bromotrimethylsilane in acetonitrile with an overall yield 48%.

U.S. Pat. No. 6,465,649 discloses a process for the preparation of (R)-9-[2-(phosphonomethoxy)propyl]adenine by dealkylation of (R)-9-[2-(Diethyl phosphonomethoxy)propyl]adenine with chlorotrimethylsilane in chloroform under pressure.

The above prior art processes describe the processes involves the usage of highly corrosive and expensive reagents like bromotrimethylsilane and chlorotrimethylsilane which require special handling procedures. Such differences provide a compelling basis to develop simple dealkylation procedure for Phosphonate ester with improved yields without using expensive reagents like trialkylsilylhalides.

A number of processes for the preparation of Tenofovir disoproxil have been disclosed. In all the prior art references Tenofovir disoproxil is converted to its fumarate salt without isolating the pure Tenofovir disoproxil base.

The process mentioned above have the disadvantage that it is difficult to separate the intermediates formed during the process, from the end product and, accordingly, extensive purification procedures are required in order to obtain the necessary quality of the end product.

It is also observed that while storing Tenofovir disoproxil in liquid state it is being converted to mono ester of Tenofovir which leads lowering the yield of final product with inferior quality.

It has now been found that base of Tenofovir disoproxil may be obtained as pure and crystalline product, which may be easily handled and conveniently be converted into other pharmaceutically accepted salts.

OBJECT OF THE INVENTION

The main object of the present invention is to provide hemifumarate salt of Tenofovir disoproxil.

Another object of the present invention is to provide a process for the preparation of Tenofovir disoproxil hemifumarate.

Yet another object of the present invention is to provide a process for the preparation of (R)-9-[2-(phosphonomethoxy)propyl]adenine.

Another object of the present invention is to provide a process for the preparation of (R)-9-[2-(phosphonomethoxy)propyl]adenine without using Trialkylsilylhalides.

Further object of the present invention is to provide a process for the preparation of (R)-9-[2-(phosphonomethoxy)propyl]adenine by using mineral acids.

In yet another object of the present invention is to provide a process for the preparation of (R)-9-[2-(phosphonomethoxy)propyl]adenine with improved yield. Another object the invention relates to the pure crystalline base of Tenofovir disoproxil.

SUMMARY OF THE INVENTION

The present invention relates to novel Tenofovir disoproxil hemifumarate salt, which is prepared by dealkylation of Phosphonate esters by using mineral acids followed by esterification and crystallization to give crystalline Tenofovir disoproxil. The Tenofovir disoproxil is further converted to fumarate salts with improved yield.

DETAILED DESCRIPTION OF THE INVENTION

The inventors have found a new salt of Tenofovir disoproxil, the hemifumarate salt. Tenofovir disoproxil hemifumarate is prepared by dealkylating (R)-9-[2-(Diethyl phosphonomethoxy)propyl]adenine to give Tenofovir which is condensed with chloromethyl isopropyl carbonate to get crystalline Tenofovir disoproxil which is optionally isolated. The crystalline tenofovir disoproxil is treated with stoichiometric equivalent of fumaric acid to obtain hemifumarate. The hemifumarate obtained is isolated by conventional techniques.

In another aspect, Tenofovir disoproxil hemifumarate can be prepared by dissolving Tenofovir disoproxil fumarate in a suitable solvent followed by cooling the solution and isolating the product by the conventional methods.

In another aspect Tenofovir disoproxil hemifumarate is prepared by converting Tenofovir disoproxil fumarate to Tenofovir disoproxil and treating Tenofovir disoproxil with stoichiometric equivalent quantity of fumaric acid in a suitable solvent and isolating the product by the conventional methods.

The new salt is characterized by its infrared spectrum and X-ray powder diffraction pattern as shown in FIGS. 1B and 2B, respectively.

The PXRD spectrum of hemi-fumarate is characterized by the following peaks with 2θ angle positions at about 2 θ 7.8, 8.0, 9.8, 10.5, 10.9, 11.9, 13.6, 14.2, 14.6, 16.0, 16.7, 17.2, 17.9, 18.4, 19.1, 20.3, 21.1, 21.6, 22.5, 23.3, 24.2, 25.2, 26.3, 26.7, 27.0, 28.5, 29.7, 30.3, 31.1, 31.9, 32.8, 34.7±0.2

The Fumaric acid content in the hemifumarate salt was analyzed by chemical analysis and found to be 10.2.

In another embodiment the present invention is directed towards the dealkylation step in the preparation of Tenofovir by the use of mineral acids in aq media and alcohols in place of trialkylsilylhalides used in the prior art. The process in present invention is cost effective, industrially applicable, uses less cumbersome steps and advantageous over the prior art processes where trialkylsilylhalides are employed for dealkylation. The following scheme shows the preparation of Tenofovir

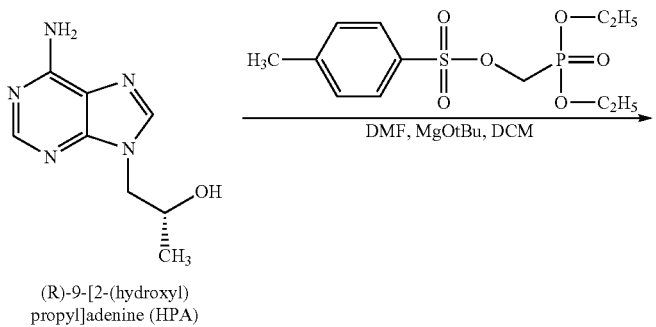

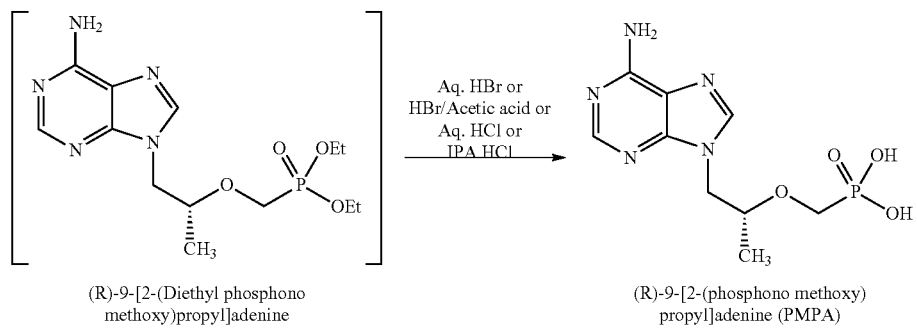

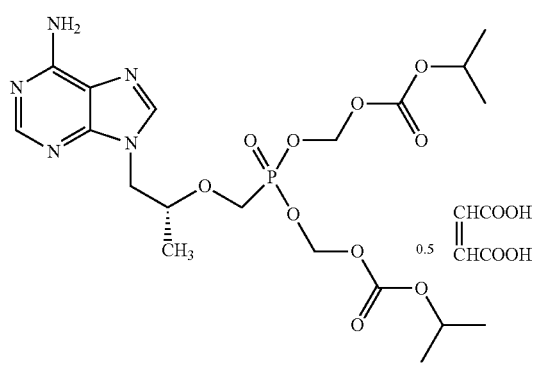

Tenofovir disoproxil fumarate

-continued

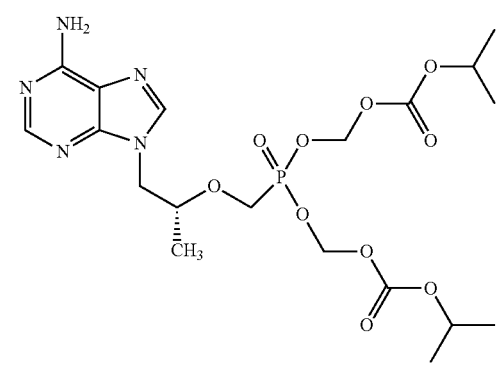

9-[-2-(R)-[[bis[[(isopropoxycarbonyl)
oxy]methoxy]phosphinoyl]methoxy]
propyl]adenine-Tenofovir Disoproxil Base The preparation of (R)-9-[2-(phosphonomethoxy)propyl] adenine comprises the steps of:

i) Reacting (R)-9-[2-(hydroxyl)propyl]adenine with diethyl p-toluenesulfonyloxy methylphosphonate in presence of Magnesium tert-butoxide to get (R)-9-[2-(Diethyl phosphonomethoxy)propyl]adenine ii) Dealkylation of (R)-9-[2-(Diethyl phosphonomethoxy) propyl]adenine with mineral acid(s)

iii) Isolation and drying the product to get (R)-9-[2-(phosphonomethoxy)propyl]adenine Accordingly (R)-9-[2-(hydroxyl)propyl]adenine is condensed with Diethyl p-toluene sulfonyloxy methylphosphonate in presence of Magnesium tert-butoxide in a polar solvent preferably dimethylformamide at a temperature of 70° C. to 80° C. After the reaction completion the reaction mass is neutralized by adding an acid preferably acetic acid and the solvent is distilled off completely. The obtained crude is dissolved in a chlorinated hydrocarbon selected from Methylenedichloride, chloroform, and Ethylene dichloride and water is added. The reaction mixture is filtered to remove the salts and Methylenedichloride layer is separated. Methylenedichloride is distilled off completely to get (R)-9-[2-(phosphonomethoxy)propyl]adenine.

Dealkylation of (R)-9-[2-(Diethyl phosphonomethoxy) propyl]adenine is carried out in presence of a suitable dealkylating reagents selected from mineral acids like aq. HBr, aq. HCl, HBr in acetic acid or HCl gas in IPA with mole ratio ranging from 3 to 15 preferably 7.5 moles and typically at a temperature of about 25 to 110° C., usually at 90 to 95° C. (R)-9-[2-(Diethyl phosphonomethoxy)propyl]adenine and one of the acid described above are maintained at 90 to 95° C. for about 3 to 15 hrs, after completion of reaction, the reaction mass is washed with Methylenedichloride and pH is adjusted to about 1.5 to 3.5 preferably at 2.5 to 3.0 with caustic lye solution. Reaction mass is cooled to about 25 to 35° C. and finally to about 0 to 5° C. over 4 to 10 hrs. The precipitated product is filtered and the wet material is recrystallized in water to get pure (R)-9-[2-(phosphonomethoxy)propyl]adenine with improved yield.

The required (R)-9-[2-(hydroxyl) propyl]adenine is prepared by the prior art methods.

In further embodiment the present invention describes preparation of Tenofovir disoproxil fumarate comprising i) Treating Tenofovir with chloromethyl isopropyl carbonate (CMIC) in an organic solvent in presence of a base, ii) Isolating the crystalline Tenofovir disoproxil, iii) Treating Tenofovir disoproxil with fumaric acid in an solvent, iv) Optionally seeding with Tenofovir disoproxil fumarate and v) Isolating Tenofovir disoproxil fumarate In a specific embodiment of the present invention Tenofovir is reacted with chloromethyl isopropyl carbonate in an organic solvent in presence of a base at a temperature of room temperature to 80° C. The obtained Tenofovir disoproxil is crystallized in a suitable organic solvent selected from hydrocarbons, esters, alkanols and mixtures thereof. The crystalline free base of Tenofovir disoproxil is isolated from the reaction mass at suitable temperature preferably at low temperatures.

The obtained Tenofovir disoproxil is further converted to pharmaceutically acceptable salts, preferably fumarate salt as per the prior art methods.

The crystalline base of Tenofovir disoproxil is preferably more than 90.0% pure, more preferably more than 95.0% w/w (peak area). The melting point is preferably a range within (DSC: onset, open capsule) 86-104° C. or it is between 87 and 103° C.

The crystalline Tenofovir disoproxil is further characterized by PXRD spectrum having the following peaks with 2θ angle positions at about 4.8, 5.4, 7.8, 8.0, 10.3, 13.6, 14.6, 15.4, 16.6, 17.2, 18.5, 19.4, 20.0, 20.7, 21.1, 21.6, 22.2, 22.7, 24.3, 24.8, 27.2, 29.3, 34.5.±0.2.

The base of Tenofovir disoproxil may also be set free from the salt of Tenofovir disoproxil by dissolving the crude salt in a mixture of water and an organic solvent and then adding a base. The organic solvent may be toluene, ethyl acetate or any other suitable solvent and the base may be any convenient base, preferably $NaHCO_3$ or $NH_3$. The base of Tenofovir disoproxil is collected by the separation of the organic phase, evaporation of the solvent in order to obtain the base most probably as an oil and then crystallization of the base from an organic solvent.

The term crude salt refers to the fact that the salt comprises impurities, which must be removed or which it is desired to remove. The crude salt may be a salt separated directly from the reaction mixture, or it may have been subjected to some initial purification, e.g. one re-crystallization. This salt may be prepared by any of the above mentioned processes and it might be obtained directly by the reaction or it may be formed subsequently by treatment with an acid.

Pharmaceutically acceptable salt of Tenofovir disoproxil, such as fumarate may be prepared by methods known in the art. So the base may be reacted with either the calculated amount of acid in a water miscible solvent, with subsequent isolation of the salt. The fumarate salt of the Tenofovir disoproxil obtained by the method of the invention has a very high purity, preferably more than 99.0%, most preferably more than 99.5% purity. Other salts of the Tenofovir disoproxil may also be obtained in a very pure form by this process.

According to the present invention, the base of Tenofovir disoproxil has been found to be crystalline with stable and white crystals and it has been found that the base may easily be crystallized in a very pure form. Accordingly, the process of the invention for preparing salts of Tenofovir disoproxil has been found to give the salts as very pure products of pharmaceutically acceptable quality.

BRIEF DESCRIPTION OF THE DRAWINGS

The invention will now be described in further detail with reference to the drawings, wherein FIG. 1 consists of two IR spectra, wherein FIG. 2: consists of two X-ray difractograms, wherein FIG. 3: consists of two thermograms, wherein

Preparation of Tenofovir Disoproxil Hemifumarate

Example-1

Figure 1A:
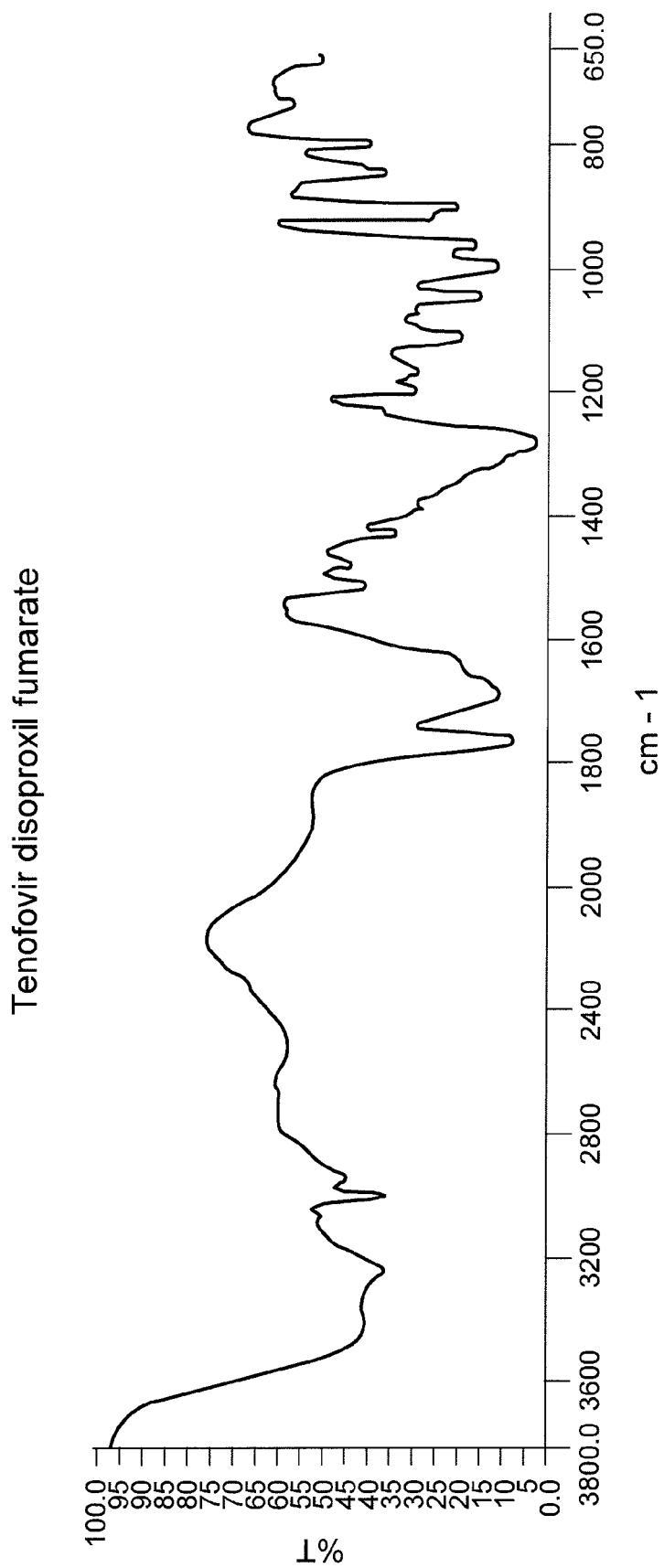
FIG. 1A is the IR spectrum of Tenofovir disoproxil fumarate.

Tenofovir disoproxil fumarate (100 gms, 0.1574 moles) is suspended in Isopropyl alcohol (1100 ml) at 25-35° C. The suspension is heated to about 60° C. for clear solution. The obtained clear solution is maintained for 1 hr at 60-65° C. Slowly cooled the mass to 30° C. in 1 hr and again cooled to 8° C. and maintained for ½ hr at 8-10° C. The precipitated product is filtered and washed with chilled Isopropanol. The wet material is dried at 50-55° C. under vacuum to give Tenofovir disoproxil hemifumarate.
Yield: 82.0 Gms
Fumaric acid content: 10.2%

Example-2

Tenofovir disoproxil fumarate (100 gms, 0.1574 moles) is suspended in DM water (500 ml) and ethyl acetate (500 ml) at 25-35° C. and adjusted pH to neutral with saturated Sodium bicarbonate solution. Reaction mixture is settled and the separated ethyl acetate layer is evaporated under vacuum below 45° C. to get Tenofovir disoproxil as residue.

In another flask Fumaric acid (9.12 gm, 0.0786 moles) is suspended in Isopropyl alcohol (1200 ml) at 25-35° C. and raised the temperature to 50° C. To the obtained solution Tenofovir disoproxil residue is added and maintained for 1 hr at 50° C. The reaction mass is cooled to 25-35° C. and maintained for 2 hrs. The reaction mass is cooled to cooled to 10° C. and maintained for 4 hrs. The crystallized product is filtered and washed with Isopropyl alcohol (100 ml). The wet material is dried at 50-55° C. under vacuum to give Tenofovir disoproxil hemifumarate.
Yield: 87.0 gms
Fumaric acid content: 10.2%

Example 3

Preparation of (R)-9-[2-(phosphonomethoxy)propyl]adenine (R)-9-[2-(hydroxyl)propyl]adenine (100 gm, 0.518 mol) was suspended in dimethylformamide (200 ml) at 25-35° C. and added Magnesium tert-butoxide (71 gm, 0.415 mol), heated to 60° C., maintained for 1 hr, raised the temperature to 74° C., added diethyl p-toluenesulfonyloxymethyl phosphonate (200 gm, 0.6216 mol) in 21 hrs 74-78° C., maintained for 5 hrs at that temperature, cooled to 25-35° C., Acetic acid (60 gm, 1.0 mol) was added. Distilled off the solvent completely under vacuum at below 80° C., cooled to 25-35° C., charged methylenedichloride (600 ml), water (100 ml), filtered the salts and separated the layers. Distilled off methylenedichloride, added aq. HBr (655 gm, 3.88 mol), heated to 90° C., maintained for 5 hrs, cooled to RT, charged Water (300 ml) and methylenedichloride (300 ml), maintained for 1 hr, adjusted the aq. layer pH to 2.5 to 3.0 with Caustic lye, cooled to 5° C., maintained for 4 hrs, filtered the mass. Wet cake heated to reflux with water for dissolution, cooled to RT, finally to 5° C., filtered the material, washed with water and dried the material.

The dry weight of (R)-9-[2-(phosphonomethoxy)propyl]adenine is 110 gms (Yield 70%).

Example 4

Preparation of (R)-9-[2-(phosphonomethoxy)propyl]adenine (R)-9-[2-(hydroxyl)propyl]adenine (100 gm, 0.518 mol) was suspended in dimethylformamide (200 ml) at 25-35° C. and added magnesium tert-butoxide (71 gm, 0.415 mol)) and heated to 60° C., maintained for 1 hr, raised the temperature to 74° C., added Diethyl p-toluenesulfonyloxymethylphosphonate (200 gm, 0.6216 mol) in 2 hrs 74-78° C., maintained for 5 hrs at that temperature, cooled to 25-35° C., added acetic acid (60 gm, 1.0 mol). Distilled off the solvent completely under vacuum at below 80° C., cooled to 25-35° C., charged methylenedichloride (600 ml), water (100 ml), filtered the salts and separated the layers. Distilled off Methylenedichloride. Added HBr/acetic acid (24%) (610 gms, 3.5 mol), heated to 55° C., maintained for 10 hrs, cooled to 25 to 30° C., charged DM water (300 ml) and methylenedichloride (300 ml), maintained for 1 hr, adjusted the aq. layer pH to 2.5 to 3.0 with Caustic lye, cooled to 5° C., maintained for 4 hrs and filtered the mass. The wet cake heated to reflux with water for dissolution, cooled to RT, finally to 5° C. and filtered the material, washed with water and dried the material.

The dry weight of (R)-9-[2-(phosphonomethoxy)propyl]adenine is 90 gms (Yield 60%).

Example-5

Preparation of Tenofovir Disoproxil

Tenofovir (100 gms) and cyclohexane (800 ml) are added at 25-35° C. under nitrogen. Temperature of the reaction mixture is raised to reflux and water is separated by azeotropic distillation. Solvent is distilled off completely under vacuum. The reaction mass is cooled to 25-35° C., added NMPO (300 ml) and stirred for 30 min at 25-35° C. Triethylamine (100 gms) is added to the reaction mass at 25-35° C. and stirred for 1 hr at 25-35° C. Reaction mass is heated to 54-58° C. and CMIC (250 gms) is added at 54-58° C. and maintained at 54-58° C. for 5 hrs. Reaction mass is cooled to room temperature and ethyl acetate (400 ml) is added. Reaction mass is cooled to 10-15° C. and stirred for 1 hr at 10-15° C. The salts are filtered and washed with ethyl acetate (200 ml). To the filtrate ethyl acetate (1200 ml) is added and washed with purified water (600+600+300 ml) at 10-15° C. Ethyl acetate layer is dried over sodium sulphate and distill off completely under vacuum below 40° C. Reaction mass is cooled to 25-35° C. and cyclohexane (300 ml) is charged at 25-35° C. while reaction mass becomes thick solid. Reaction mass is stirred for 1 hr at 25-35° C. and 1 hr at 10-15° C. The precipitated product is filtered and washed with chilled cyclohexane (100 ml). The wet cake is dried under vacuum at 25-35° C. for 3 hrs to get the desired product.

Output: 135 gms
Melting point: 103-105° C.
Purity: 99.85% by HPLC

Example-6

Preparation of Tenofovir Disoproxil Fumarate

Tenofovir disoproxil (135 gms) is dissolved in methylene dichloride (600 ml) at 25-35° C. Reaction mass is cooled to 10-15° C. and washed with purified water (200+200 ml) at 10-15° C. methylene dichloride is distilled off completely under vacuum below 40° C. The obtained residue is dissolved in Isopropyl alcohol (300 ml) at 20-25° C. under nitrogen atmosphere. The obtained mass is added to a solution of Fumaric acid (38 gm dissolved in 700 ml Isopropyl alcohol) at 50-55° C. Reaction mass is stirred for 1 hr at 50-55° C. and filter through micron filter. The clear filtrate is gradually cooled to 40° C. and seeded with pure Tenofovir disoproxil fumarate. Reaction mass is slowly cooled to 30-35° C. Once the haziness is observed stirring is stopped allowed to crystallize 3 hrs. Reaction mass is slowly cooled to 25-35° C. and stirred for 1 hr at 25-35° C. Again the reaction mass is cooled to 8-12° C. and stirred for 4 hrs at 8-12° C. The crystallized product is filtered and washed with Isopropyl alcohol (200 ml). The wet product is dried under vacuum at 25-35° C. for 2 hrs and at 40-45° C. till LOD and moisture content comes within the limit (LOD: NMT 1.0%; Moisture content: NMT 1.0%)

Output: 110 gms
Purity: 99.6%

Figure 1B:
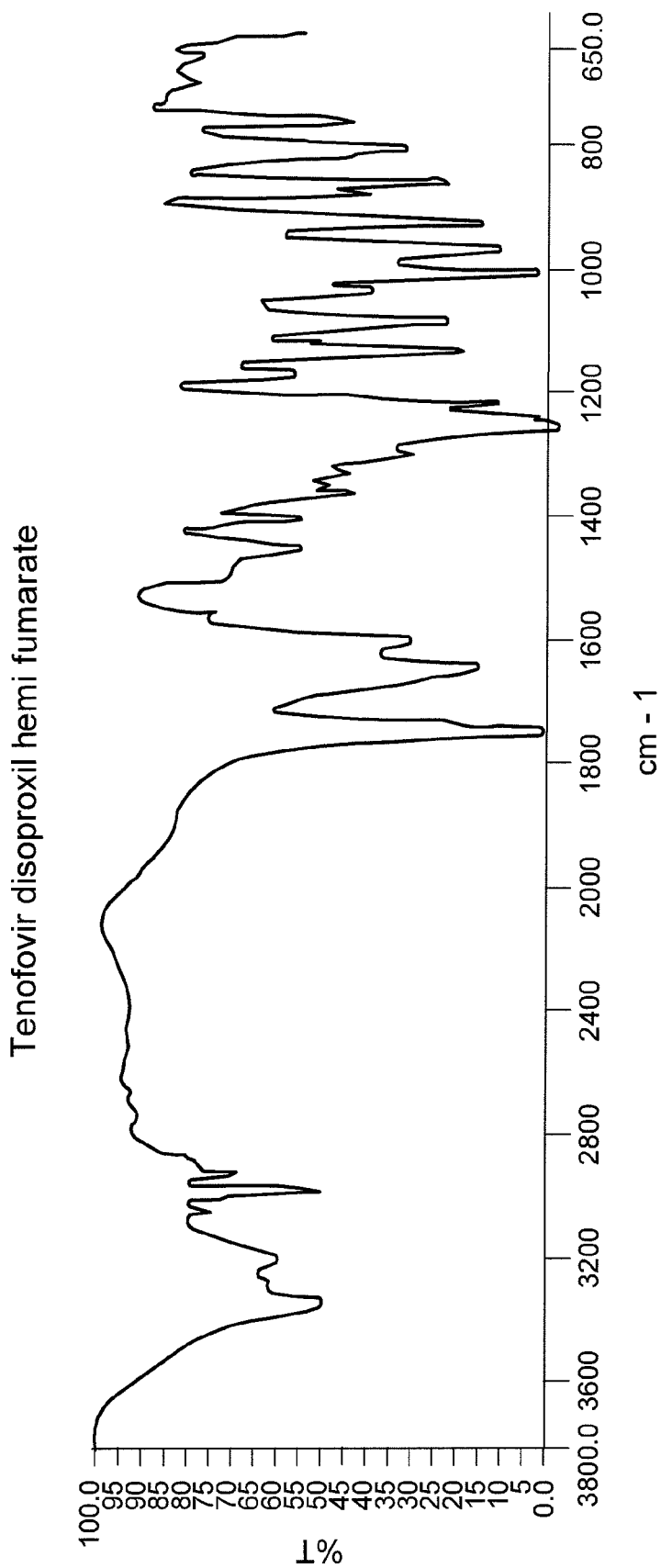
FIG. 1B is the IR spectrum of Tenofovir disoproxil hemifumarate.
Figure 2A:
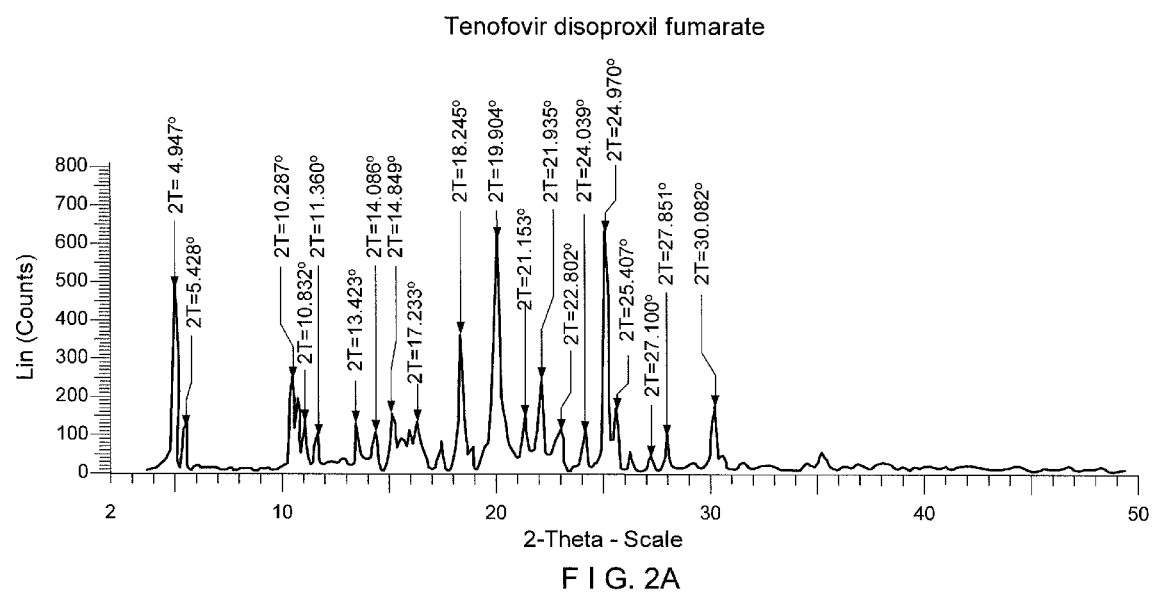
FIG. 2A is the X-ray difractogram of Tenofovir disoproxil fumarate.
Figure 2B:
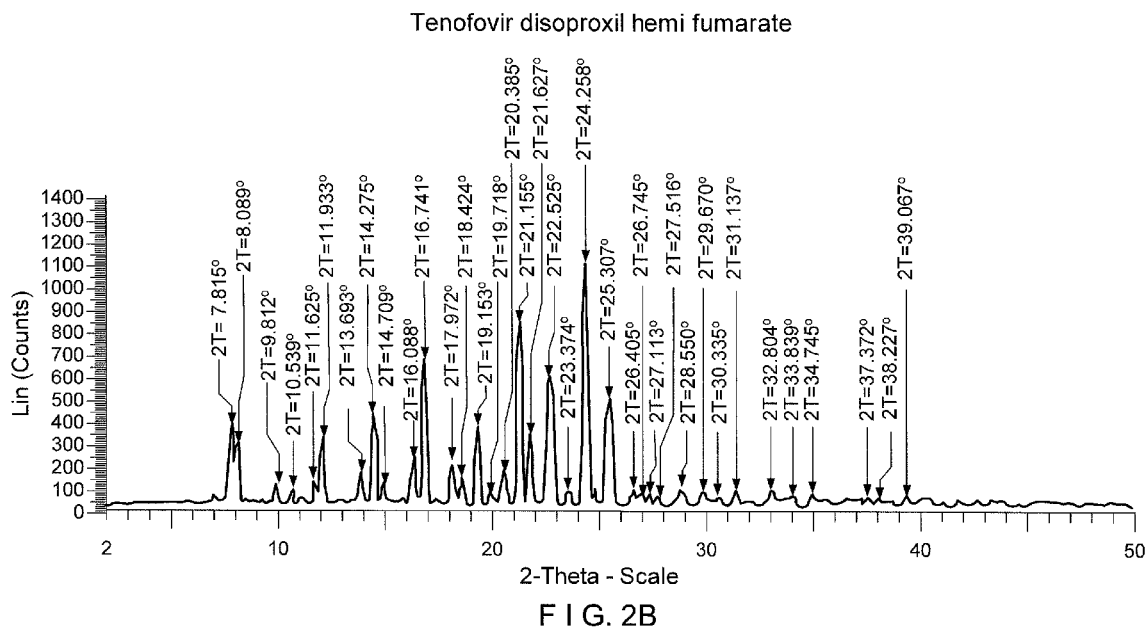
FIG. 2B is the X-ray difractogram of Tenofovir disoproxil hemifumarate.
Figure 3A:
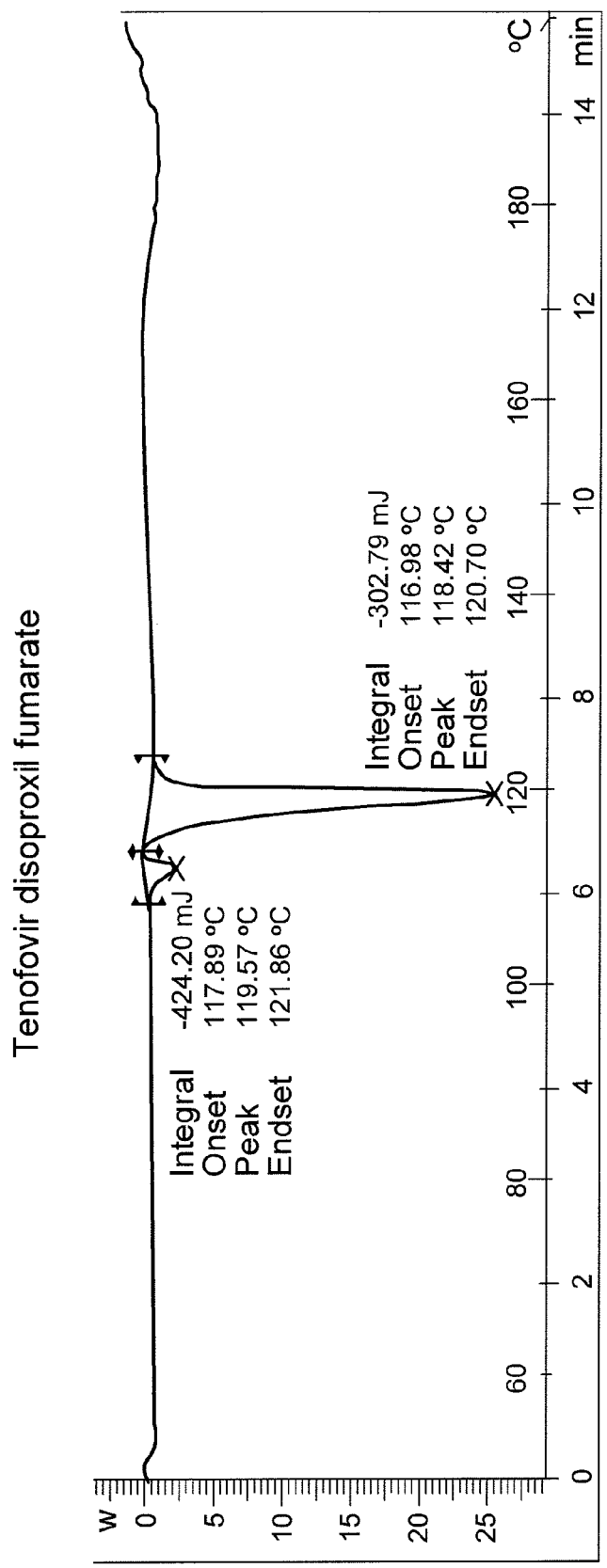
FIG. 3A is the DSC of Tenofovir disoproxil fumarate.
Figure 3B:
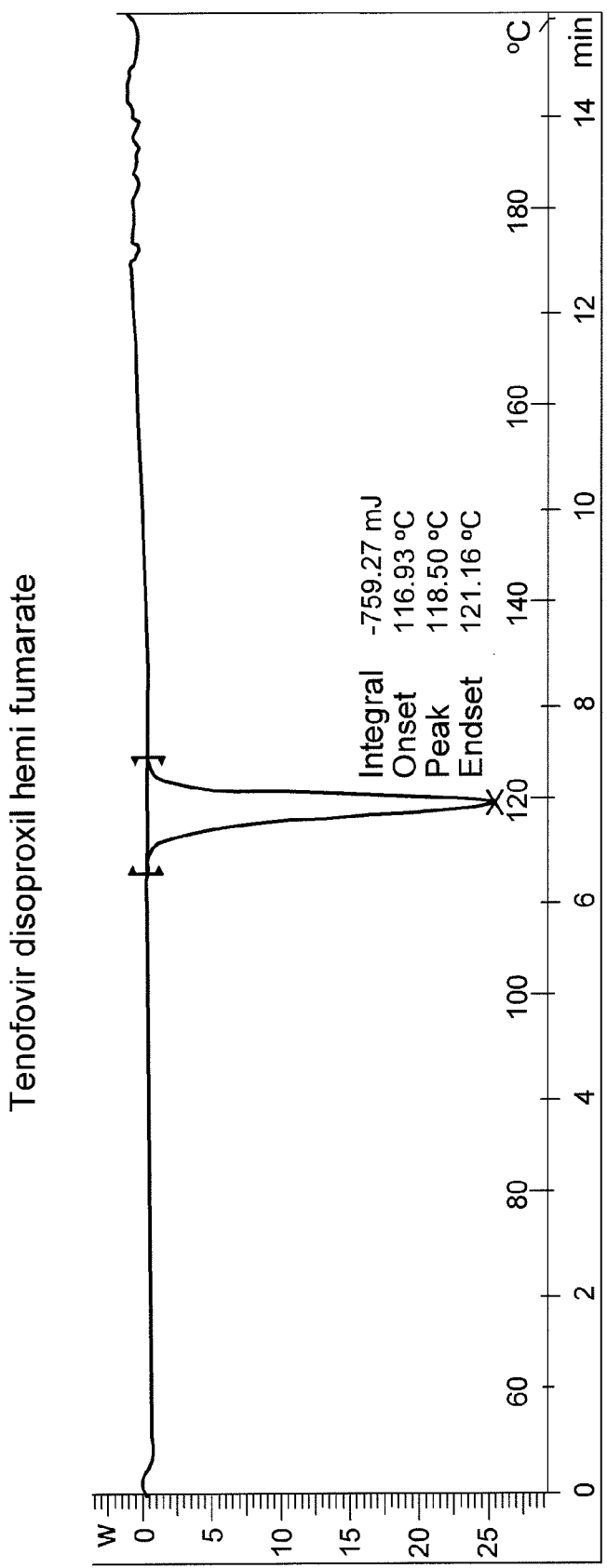
FIG. 3B is the thermogram of Tenofovir disoproxil hemifumarate.
Figure 4:
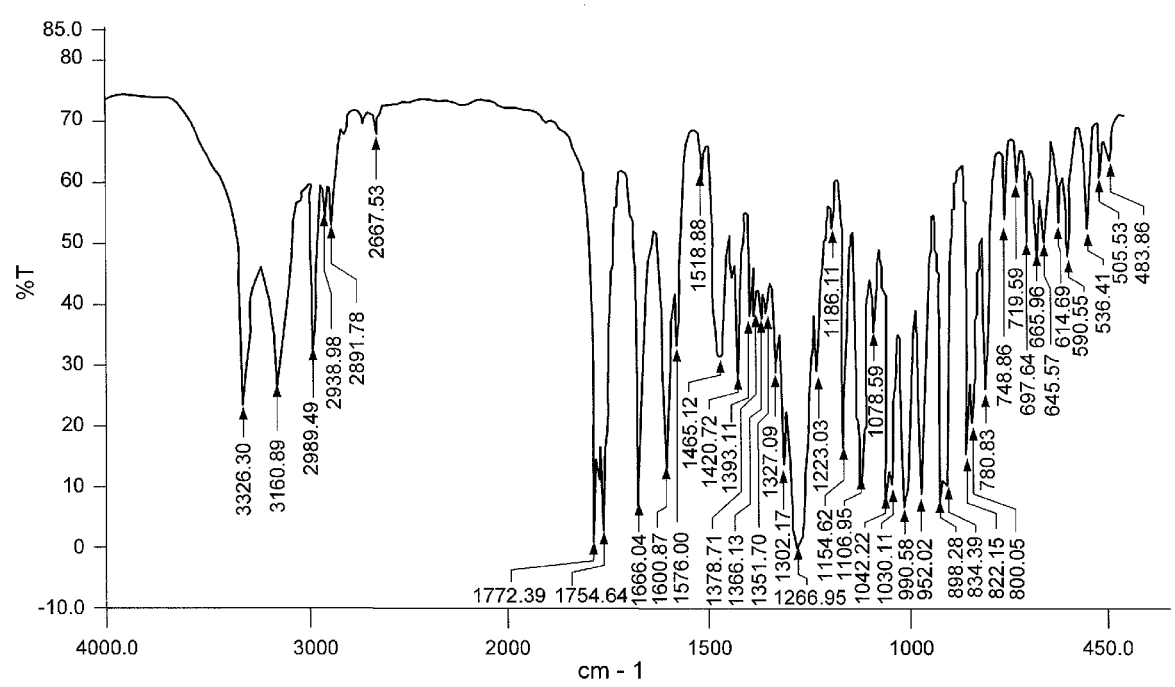
FIG. 4 is the IR spectrum of crystalline Tenofovir disoproxil
Figure 5:
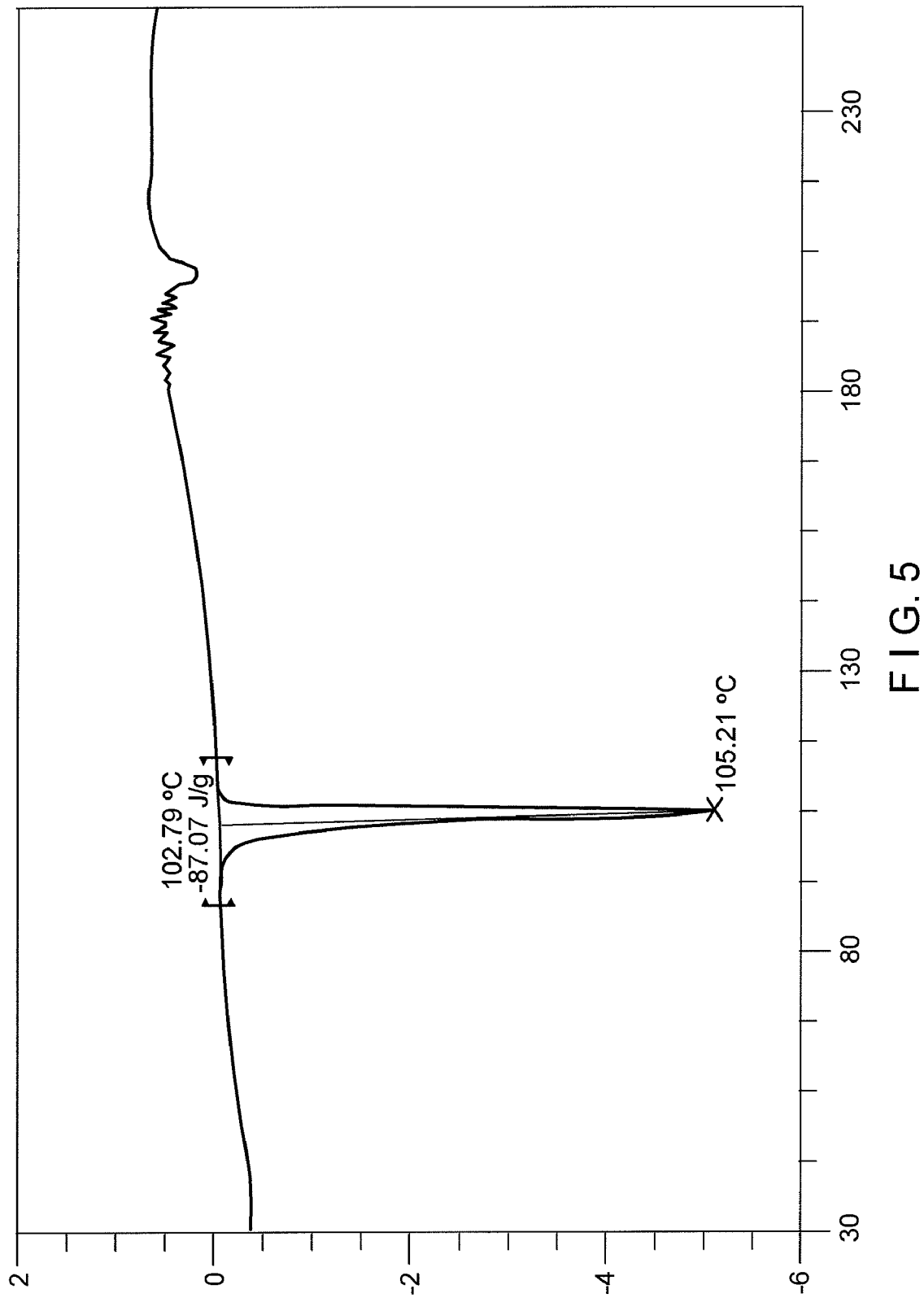
FIG. 5: is the DSC of crystalline Tenofovir disoproxil The present invention will now be further explained in the following examples. However, the present invention should not be construed as limited thereby. One of ordinary skill in the art will understand how to vary the exemplified preparations to obtain the desired results.

We claim:

1. Tenofovir disoproxil hemifumarate.
2. Tenofovir disoproxil hemifumarate according to claim 1, characterized by an IR spectrum as depicted in FIG. 1B.
3. Tenofovir disoproxil hemifumarate according to claim 1, characterized by a DSC as depicted in FIG. 3B.
4. A process for the preparation of Tenofovir which comprises:
   i) dealkylating (R)-9[2-(diethylphosphonomethoxy)propyl]adenine with a mineral acid and
   ii) isolation and drying the product to get Tenofovir.
5. The process as claimed in claim 4, wherein the mineral acid is selected from a group consisting of aq. HBr, aq. HCl, HBr in acetic acid and HCl gas in isopropyl alcohol.
6. The process as claimed in claim 4, wherein the dealkylating agent is used in a molar ratio of 3 to 15.
7. The process as claimed in claim 6, wherein the molar ratio is 7.5 to 8.5.
8. The process as claimed in claim 4, wherein the dealkylation reaction is carried out at a temperature of 25 to 110° C.
9. The process as claimed in claim 8, wherein the temperature is 90 to 95° C.
10. The process as claimed in claim 4, wherein the obtained tenofovir is further crystallized in water.
11. The process according to claim 4, further comprising the step of converting the Tenofovir to Tenofovir disoproxil and subsequently to a pharmaceutically acceptable salt thereof.
12. The process according to claim 11, wherein the pharmaceutically acceptable salt is a fumarate salt.
13. The process according to claim 4, wherein the Tenfovir is further converted into Tenofovir disoproxil fumarate.

* * * * *